United States Patent
Belluomo et al.

(10) Patent No.: US 9,925,004 B2
(45) Date of Patent: Mar. 27, 2018

(54) MICROWAVE DEVICE FOR TISSUE ABLATION

(71) Applicant: H.S.—Hospital Service S.P.A., Rome (IT)

(72) Inventors: Armando Belluomo, Rome (IT); Nevio Tosoratti, Rome (IT); Massimiliano Iacobbi, Ardea Rome (IT); Simone Cassarino, Rome (IT); Claudio Amabile, Cisterna di Latina (IT)

(73) Assignee: H.S.—Hospital Service S.P.A. (IT)

( * ) Notice: Subject to any disclaimer, the term of this patent is extended or adjusted under 35 U.S.C. 154(b) by 155 days.

(21) Appl. No.: 14/910,974

(22) PCT Filed: Jul. 31, 2014

(86) PCT No.: PCT/IB2014/063590
§ 371 (c)(1),
(2) Date: Feb. 8, 2016

(87) PCT Pub. No.: WO2015/019254
PCT Pub. Date: Feb. 12, 2015

(65) Prior Publication Data
US 2016/0199130 A1     Jul. 14, 2016

(30) Foreign Application Priority Data
Aug. 8, 2013  (IT) .............................. MO2013A0234

(51) Int. Cl.
A61B 18/18    (2006.01)
A61B 18/00    (2006.01)

(52) U.S. Cl.
CPC ...... *A61B 18/1815* (2013.01); *A61B 2018/00083* (2013.01); *A61B 2018/00577* (2013.01); *A61B 2018/1861* (2013.01); *A61B 2018/1869* (2013.01)

(58) Field of Classification Search
CPC ............... A61B 18/18; A61B 18/1815; A61B 2018/183; A61B 2018/1838; A61B 2018/1846; A61B 2018/1853; A61B 2018/1869
See application file for complete search history.

(56) References Cited

U.S. PATENT DOCUMENTS

| 2003/0052612 A1 | 3/2003 | Tanabe |
| 2003/0088242 A1 | 5/2003 | Prakash et al. |
| 2005/0085881 A1* | 4/2005 | Prakash ................. A61B 18/18 607/101 |

(Continued)

FOREIGN PATENT DOCUMENTS

| IT | MO20050034 A1 | 8/2006 |
| WO | 2006084676 A1 | 8/2006 |

*Primary Examiner* — Jaymi Della
(74) *Attorney, Agent, or Firm* — St Onge Steward Johnston and Reens LLC

(57) ABSTRACT

An antenna for a microwave device for tissue ablation includes a metal cannula inside which there are arranged an external conductor and an internal conductor of the antenna, between which a layer of electrically insulating material is interposed, and a penetrating tip connected to the antenna. The antenna further includes a reinforcing element connected to a distal end of the cannula, the penetrating tip being connected to a distal end of the reinforcing element.

5 Claims, 3 Drawing Sheets

(56) References Cited

U.S. PATENT DOCUMENTS

| | | | |
|---|---|---|---|
| 2007/0203551 A1* | 8/2007 | Cronin | A61B 18/18 607/101 |
| 2010/0318078 A1* | 12/2010 | Turovskiy | A61B 18/18 606/33 |
| 2011/0056069 A1 | 3/2011 | Bonn | |
| 2011/0060325 A1* | 3/2011 | Bonn | A61B 18/18 606/33 |
| 2011/0071511 A1* | 3/2011 | Brannan | A61B 18/1815 606/33 |
| 2012/0232619 A1 | 9/2012 | Turovskiy et al. | |

* cited by examiner

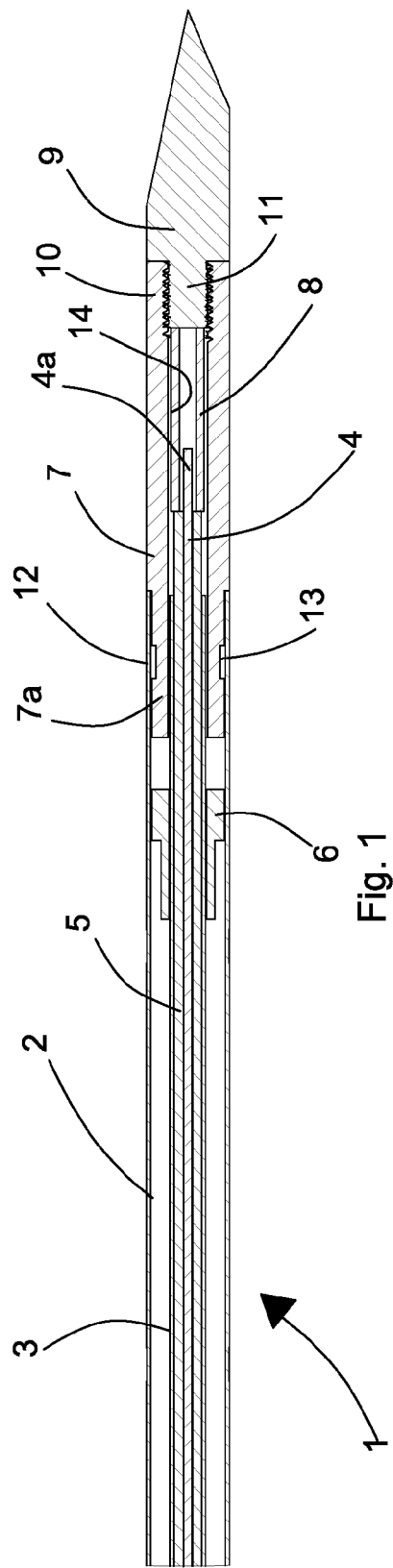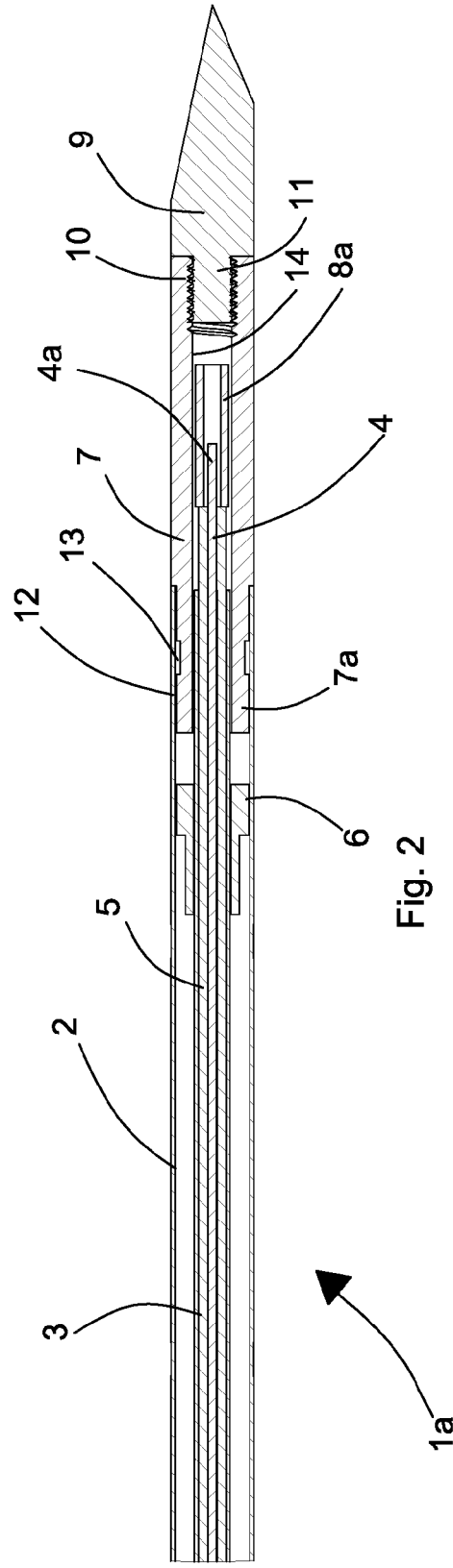

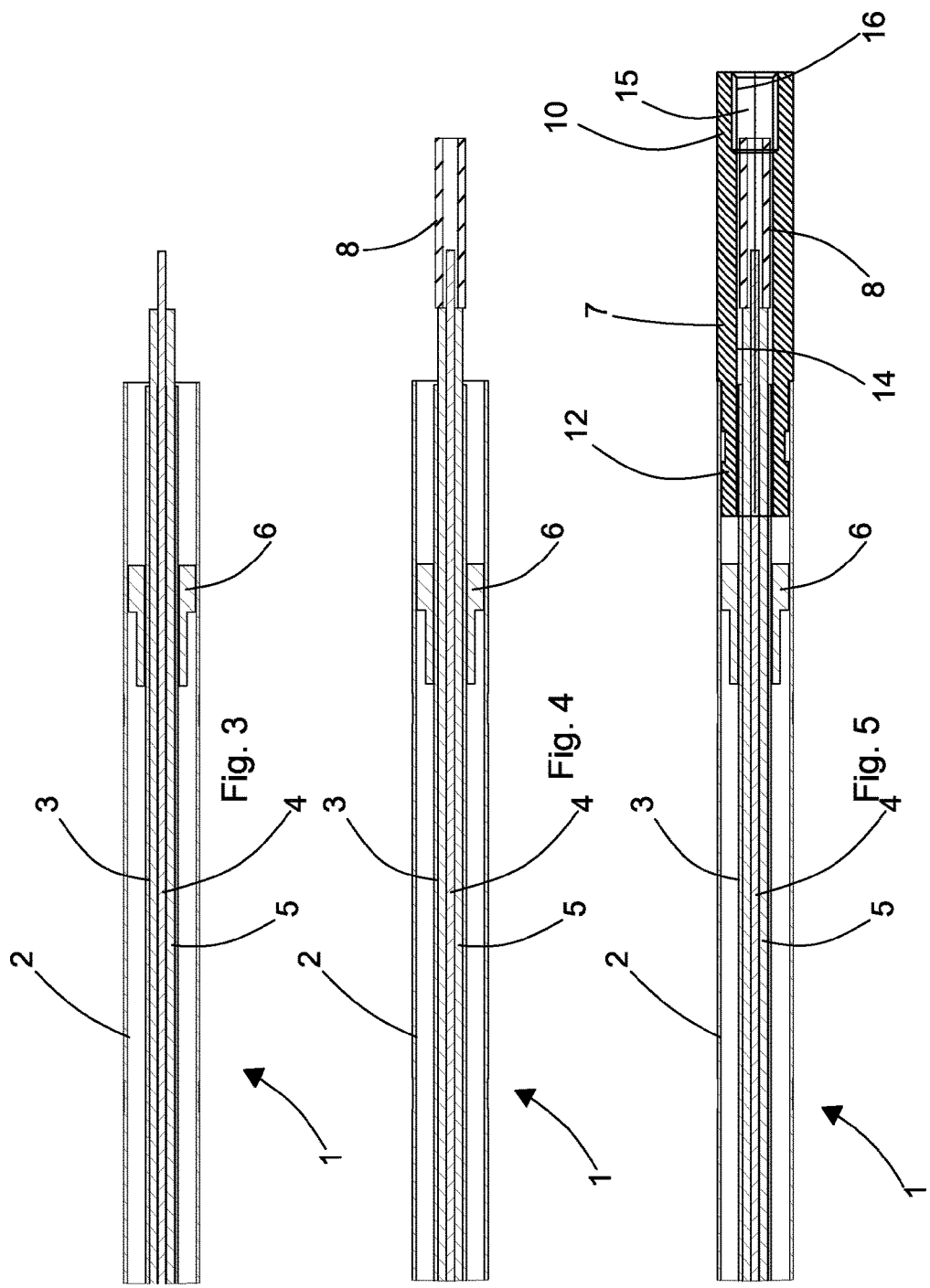

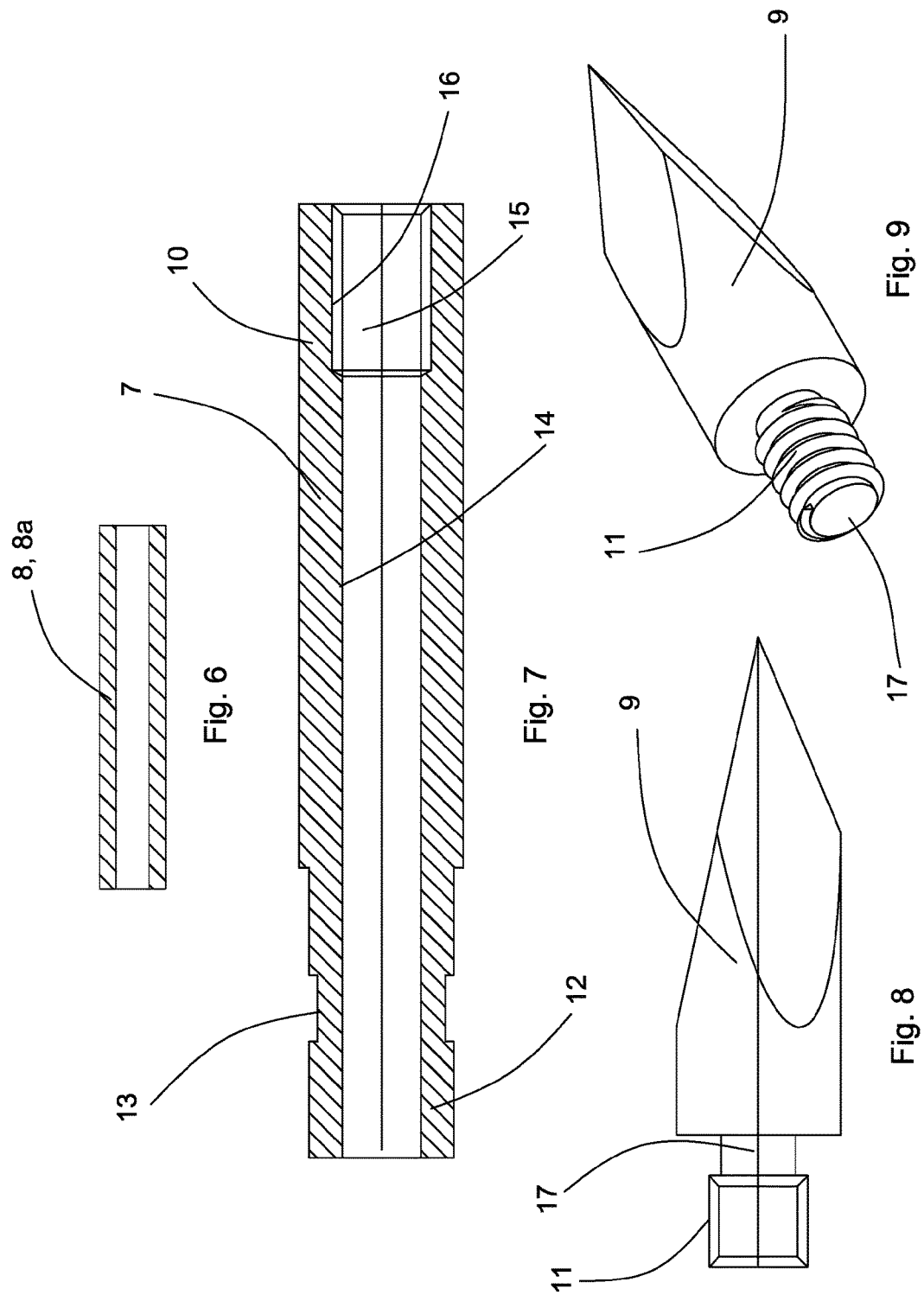

MICROWAVE DEVICE FOR TISSUE ABLATION

FIELD OF THE INVENTION

The present invention relates to a microwave device for tissue ablation, in particular a microwave interstitial applicator for hyperthermia treatment of biological tissues, in particular for thermoablation of said tissues.

BACKGROUND OF THE INVENTION

Thermoablation consists of destroying target tissues by inducing a temperature increase of the cells above an irreversible damage threshold. This threshold is linked to exposure time at a set temperature; in the case of temperatures comprised between 50° C. and 60° C. the time is of a few minutes whereas from 60° C. upwards cell death is almost instantaneous. The temperature increase is obtained by dispensing energy into the target tissues by more or less invasive applicators. The forms of energy that are commonly used for thermoablation comprise mechanical waves, radiofrequency currents, infrared radiations, microwaves.

One of the most promising forms of energy for thermoablation is currently microwave energy, which provides an excellent compromise between efficiency of transfer of energy and depth of penetration in biological tissues. The delivery of microwave energy to tissues destined for thermoablation occurs by inserting percutaneously, endoscopically, laparotomically or laparoscopically interstitial applicators consisting of a coaxial antenna comprising an internal conductor, a dielectric layer that covers the entire length of the internal conductor, an external conductor that covers coaxially the dielectric layer and the internal conductor, except for a distal end portion of the latter, constituting the radiant end of the antenna. The design of antennas for thermoablation must take into consideration certain constructional requirements linked to the use that is made thereof, in particular: biocompatibility, great mechanical resistance, spheroid coagulative necrosis, an antenna diameter that is as small as possible.

In order to ensure spheroid coagulative necrosis, the antenna needs both a radiation figure that is spheroid and a cooling system for dissipating the heat generated by the supply line of the antenna. At the operating frequencies of a microwave thermoablation system, the transit of power through the coaxial cable is characterised by great attenuation matched by heating of the coaxial cable. The generated heat could cause necrosis of the tissues in contact with the external stem of the antenna over the entire length thereof. The presence of a cooling circuit of the supply line enables heat to be removed and thus enables the eccentricity of the necrosis to be reduced.

A problem that is common to many antenna designs for microwave thermoablation is the elongation of the radiation figure along the supply line of the antenna, with resulting low sphericity. This elongation can be avoided by different improvements to the antenna project. One of the most common ways of maintaining good containment of the radiation figure is to use a device, called an electromagnetic choke, or more briefly choke, which makes a quarter-wave impedance transformer terminating in a short circuit. The choke is physically a coaxial line consisting of a cylindrical conductor that coaxially surrounds the external conductor of the antenna and it is closed thereupon in a short circuit at its proximal end, whereas it is open at its distal end. The terms "distal" and "proximal" refer to the ends of the device, or a part or component thereof, facing respectively in the direction of the tip of the antenna, or in the opposite direction.

Between the cylindrical conductor and the external conductor of the antenna, one or more sleeves made of dielectric material are interposed, to fill the entire length of the choke. The length of the choke is equal to an odd number (usually one) of quarters of the wavelength in said dielectric of the microwaves emitted by the antenna. Lengths that are different from a quarter of the wave confer on the choke less than optimum properties but are nevertheless useful for the purpose of obtaining a proximal containment, and thus pronounced sphericity of the radiation figure of the antenna. The choke is usually obtained by inserting, around the dielectric surrounding the external conductor of the antenna, a metal cylinder with an internal diameter that is equal to the external diameter of the dielectric and of a length that is such as to make an electric length that is equivalent to what has just been disclosed. The end of the metal cylinder that is furthest away from the radiant end of the antenna is short-circuited on the external conductor of the antenna, completing the structure of the choke.

A microwave device for tissue ablation of the previously mentioned type is disclosed in Italian patent for industrial invention 0001361771 in the name of the applicant.

The microwave devices for tissue ablation known from the prior art are further provided with a penetrating tip connected electrically to the internal conductor of the antenna, the function of which is to facilitate the introduction of the antenna into the tissues of a patient.

The penetrating tip has to be connected to the body of the antenna with a connection with great mechanical resistance that ensures that the tip cannot become detached from the body of the antenna because of mechanical stress that acts on the antenna during penetration and extraction of the antenna through the tissues of a patient.

Normally, the penetrating tip is connected to the body of the antenna by welding. This type of connection does not, however, ensure great resistance of the tip, which, if it is subject to great stress, may detach from the body of the antenna and remain inside the body of a patient, with all the problems that this entails.

SUMMARY OF THE INVENTION

The object of the present invention is to provide a microwave device for tissue ablation in which the distal part of the antenna, consisting of the penetrating tip, has great mechanical resistance, such as to ensure that the penetrating tip cannot detach from the body of the antenna even in cases of great mechanical stress.

The object of the invention is achieved with a microwave device for tissue ablation comprising an antenna, a metal cannula containing an external conductor and an internal conductor of the antenna with a layer of electrically insulating material located between them, a penetrating tip connected to the antenna, a reinforcing element connected to a distal end of the cannula, and the penetrating tip being connected to a distal end of the reinforcing element, the reinforcing element being provided with an axial hole a distal end of which is provided with internal threading, wherein it further comprises a bushing connected to a distal end of said antenna, said bushing being inserted into said axial hole and coming into contact with said shank of the penetrating tip.

Owing to the invention, the mechanical resistance of the penetrating tip of the antenna is considerably increased, without this negatively influencing or compromising the operation of the antenna.

BRIEF DESCRIPTION OF THE DRAWINGS

One manner of implementing the invention is disclosed below, by way of non-limiting example, with reference to the attached drawings, in which:

FIG. 1 is a longitudinal cross-sectional view of a first embodiment of a microwave device for tissue ablation comprising an antenna provided with a penetrating tip, according to the present invention;

FIG. 2 is a longitudinal cross-sectional view of a second embodiment of a microwave device for tissue ablation comprising an antenna provided with a penetrating tip, according to the present invention;

FIGS. 3, 4 and 5 are a longitudinal cross-sectional views illustrating assembly of the antenna of the microwave device according to the invention;

FIG. 6 is a longitudinal cross-sectional view of a bushing of the antenna of the microwave device according to the invention.

FIG. 7 is a longitudinal cross-sectional view of a reinforcing element of the antenna of the microwave device according to the invention.

FIG. 8 is a longitudinal elevation view of a penetrating tip of the antenna of the microwave device according to the invention.

FIG. 9 is a perspective view of a penetrating tip of the antenna of the microwave device according to the invention.

DETAILED DESCRIPTION OF THE INVENTION

In FIG. 1 there is illustrated a first embodiment of an antenna for a microwave device according to the invention.

The antenna 1 comprises a metal cannula 2 inside which there is arranged an internal conductor 4, surrounded by a layer 5 of insulating material that is in turn surrounded by an external conductor 3 that is coaxial to the internal conductor 4. A distal end portion 4a of the internal conductor 4 protrudes from a distal end of the external conductor 3, constituting the radiant end of the antenna 1.

Between the metal cannula 2 and the external conductor 3 of the antenna 1 there is arranged a bushing 6 of a conductive material that is part of a quarter wave impedance transformer, the object of which is to block the reflected microwaves to avoid indiscriminate heating of the tissues surrounding the antenna 1, also at a distance from the portion of tissue directly affected by the coagulative treatment.

The antenna 1 is completed by a penetrating tip 9 which facilitates the insertion of the antenna through the tissues of a patient until the zone of the body of the patient is reached that has to be subjected to ablation treatment via microwaves.

The penetrating tip 9 is connected to the metal cannula 2 by a reinforcing element 7, the object of which is to enable a connection with great mechanical resistance to be made between the penetrating tip 9 and the antenna 1. The reinforcing element can be made, for example, of zirconium oxide or of ceramic material. The reinforcing element 7 is provided with a proximal end 7a that can be introduced into the distal end 12 of the metal cannula 2. Said proximal end 7a is provided with a coupling arrangement 13 that has the object of facilitating coupling between the distal end 12 of the metal cannula 2 and the reinforcing element 7.

The coupling arrangement may consist of one or more circumferential grooves, as illustrated in FIGS. 1, 2, 5 and 7, or of axial incisions, or of spiral incisions, or also of ridges.

The coupling between the distal end 12 of the metal cannula 2 and the proximal end 7a of the reinforcing element 7 can be by mechanical crimping, or gluing in the zone of the proximal end 7a where the coupling arrangement 13 is present, i.e. the grooves, incisions or ridges. The coupling between the metal cannula 2 and the proximal end 7a of the reinforcing element 7 can also be achieved by welding. In this case, however, the proximal end 7a of the reinforcing element 7 has to be metallised to enable welding to be performed. In all cases, the connection between the cannula 2 and the reinforcing element 7 ensures great mechanical resistance against detachment of the reinforcing element 7 from the cannula 2.

The reinforcing element 7 is provided with an axial bore or hole 14 that extends over the entire length of the reinforcing element 7 from the proximal end 7a to a distal end 10. The distal end 15 of the axial hole 14 is provided with internal threading 16.

The penetrating tip 9 is provided with a shank 11 provided with an external thread 17. The shank 11 of the penetrating tip 9 can be screwed in the distal end 15 of the axial hole 14, thus making a connection with great resistance to traction that greatly reduces the risk of the penetrating tip 9 being able to detach from the antenna 1 because of mechanical stress to which it is subjected during introduction into, and extraction from, the body of a patient.

The antenna 1 is further provided with a metal bushing 8, 8a, which is connected to the distal end of the antenna 1 (FIG. 4) and is inserted into the axial hole 14 of the reinforcing element 7, when the latter is coupled with the cannula 2 (FIG. 5).

In a first embodiment, the bushing 8 has a length that is such as to come into contact with the threaded shank 11 of the penetrating tip 9 (FIG. 1), thus achieving electrical continuity between the antenna 1 and the penetrating tip 9.

In a second embodiment, the bushing 8a does not come into contact with the threaded shank 11 of the penetrating tip 9 (FIG. 2), which enables the operating temperature of the penetrating tip 9 to be reduced.

In the practical embodiment, the materials, dimensions and constructional details can be different from those indicated but be technically equivalent thereto without thereby falling outside the scope of the present invention.

The invention claimed is:

1. A microwave device for tissue ablation comprising an antenna, a metal cannula inside which there are arranged an external conductor and an internal conductor of the antenna between which a layer of electrically insulating material is interposed, a reinforcing element directly connected to a distal end of said metal cannula wherein a proximal end of said reinforcing element is inserted into said metal cannula and connected to said metal cannula by a coupling arrangement, said reinforcing element having an axial bore extending therethrough from said proximal end to a distal end of said reinforcing element, said reinforcing element being made of ceramic material, a distal end of said axial bore being provided with internal threading, a distal end of said antenna being inserted into said axial bore of said reinforcing element, a penetrating tip directly connected to a distal end of said reinforcing element, said penetrating tip being provided with a shank provided with an external thread, said shank being screwed in the distal end of said axial bore of said reinforcing element, and a conductive bushing connected to a distal end of said antenna, said conductive bushing being inserted into said reinforcing element axial bore and directly contacting the penetrating tip achieving electrical continuity between the antenna and the penetrating tip.

2. The microwave device according to claim 1, wherein said coupling arrangement comprises one or more circumferential grooves, or one or more axial incisions, or one or more spiral incisions, or ridges.

3. The microwave device according to claim 1, wherein said reinforcing element is crimped or glued to said metal cannula.

4. The microwave device according to claim 1, wherein said reinforcing element is welded to said metal cannula, said proximal end of said reinforcing element being metallised.

5. The microwave device according to claim 1, wherein said ceramic material comprises zirconium dioxide.

\* \* \* \* \*